United States Patent [19]

Azari et al.

[11] Patent Number: 5,741,894
[45] Date of Patent: Apr. 21, 1998

[54] PREPARATION OF PHARMACEUTICAL GRADE HEMOGLOBINS BY HEAT TREATMENT IN PARTIALLY OXYGENATED FORM

[75] Inventors: Mahmood Rezazadeh Azari, Gurnee; August A. Ebeling, Palatine; John E. Picken, Village of Lakewood; Timothy N. Estep, Grayslake, all of Ill.

[73] Assignee: Baxter International, Inc., Deerfield, Ill.

[21] Appl. No.: 532,293

[22] Filed: Sep. 22, 1995

[51] Int. Cl.$^6$ .................................................. C07K 14/805
[52] U.S. Cl. ........................................... 530/385; 514/6
[58] Field of Search ................................. 514/6; 530/385

[56] References Cited

U.S. PATENT DOCUMENTS

| | | | |
|---|---|---|---|
| 3,864,478 | 2/1975 | Bonhard | 424/101 |
| 3,959,128 | 5/1976 | Harris | 210/24 |
| 3,991,181 | 11/1976 | Doczi | 424/101 |
| 4,059,512 | 11/1977 | Harris | 210/24 |
| 4,291,020 | 9/1981 | Tabor et al. | 424/89 |
| 4,314,997 | 2/1982 | Shanbrom | 424/101 |
| 4,370,264 | 1/1983 | Kotitshke et al. | 260/112 |
| 4,376,727 | 3/1983 | Sato et al. | 260/112 B |
| 4,381,239 | 4/1983 | Chibata et al. | 210/679 |
| 4,438,098 | 3/1984 | Tabor et al. | 424/89 |
| 4,439,357 | 3/1984 | Bonhard et al. | 260/112 B |
| 4,440,679 | 4/1984 | Fernandes et al. | 260/122 |
| 4,456,590 | 6/1984 | Rubinstein | 424/101 |
| 4,465,774 | 8/1984 | Huang et al. | 436/15 |
| 4,473,494 | 9/1984 | Tye | 260/112 B |
| 4,526,715 | 7/1985 | Kothe et al. | 260/112 B |
| 4,540,573 | 9/1985 | Neurath et al. | 424/85 |
| 4,598,064 | 7/1986 | Walder | 514/6 |
| 4,623,717 | 11/1986 | Fernandes et al. | 530/380 |
| 4,632,980 | 12/1986 | Zee et al. | 530/380 |
| 4,764,279 | 8/1988 | Tayot et al. | 210/656 |
| 4,774,178 | 9/1988 | Egerer et al. | 435/41 |
| 4,808,314 | 2/1989 | Karplus et al. | 210/638 |
| 4,831,012 | 5/1989 | Estep | 514/6 |
| 4,841,023 | 6/1989 | Horowitz | 530/351 |
| 4,857,636 | 8/1989 | Hsia | 530/385 |
| 4,861,867 | 8/1989 | Estep | 530/385 |
| 4,886,755 | 12/1989 | Ngo | 435/183 |
| 4,909,940 | 3/1990 | Horowitz et al. | 210/634 |
| 4,925,574 | 5/1990 | Hsia | 210/635 |
| 5,011,695 | 4/1991 | Dichtelmuller et al. | 424/529 |
| 5,084,558 | 1/1992 | Rausch et al. | 530/385 |
| 5,115,100 | 5/1992 | Wu et al. | 530/385 |
| 5,189,146 | 2/1993 | Hsia | 530/385 |
| 5,204,451 | 4/1993 | Chang | 530/413 |
| 5,264,555 | 11/1993 | Shorr | 530/385 |
| 5,281,579 | 1/1994 | Estep | 514/6 |
| 5,296,465 | 3/1994 | Rausch et al. | 514/6 |
| 5,300,433 | 4/1994 | Hrinda et al. | 435/238 |
| 5,364,932 | 11/1994 | Hsia | 530/385 |
| 5,386,014 | 1/1995 | Nho et al. | 530/385 |
| 5,407,579 | 4/1995 | Lee et al. | 210/634 |
| 5,439,591 | 8/1995 | Pliura et al. | 210/635 |
| 5,439,882 | 8/1995 | Feola et al. | 514/6 |
| 5,464,814 | 11/1995 | Sehgal et al. | 514/6 |

FOREIGN PATENT DOCUMENTS

| | | |
|---|---|---|
| 622610 | 4/1992 | Australia. |
| 1187410 | 5/1985 | Canada. |
| 1312009 | 12/1992 | Canada. |
| 2049275 | 2/1993 | Canada. |
| 0035204 | 9/1981 | European Pat. Off.. |
| 0333474 | 9/1989 | European Pat. Off.. |
| 0277289 | 4/1992 | European Pat. Off.. |
| 6-11702 | 10/1981 | Japan. |
| 57-054121 | 3/1982 | Japan. |
| 60-16693 | 1/1994 | Japan. |
| 61-05686 | 4/1994 | Japan. |
| 9501034 | 12/1995 | South Africa. |
| 8700177 | 1/1987 | WIPO. |
| 8707832 | 12/1987 | WIPO. |
| 8803408 | 5/1988 | WIPO. |
| 8906969 | 8/1989 | WIPO. |
| 9015613 | 12/1990 | WIPO. |
| 9109615 | 7/1991 | WIPO. |
| 9113156 | 9/1991 | WIPO. |
| 9202239 | 2/1992 | WIPO. |
| 9204031 | 3/1992 | WIPO. |
| 9222646 | 12/1992 | WIPO. |
| 9325071 | 12/1993 | WIPO. |
| 9409027 | 4/1994 | WIPO. |
| 9504744 | 2/1995 | WIPO. |
| 9508574 | 3/1995 | WIPO. |
| 9513125 | 5/1995 | WIPO. |
| 9514038 | 5/1995 | WIPO. |
| 9524213 | 9/1995 | WIPO. |

OTHER PUBLICATIONS

Bechtel et al. Virus Removal or Inactivation in Hemoglobin Solutions by Ultrafiltration or Detergent/Solvent Treatment, Biomat., Art. Cells, Art. Org., vol. 16, Nos. 1–3, 123–128, 1988.

Biondi et al. Evaluation of Absorption with Limulus Amebocyte Lysate to Remove Contaminating Endotoxin from Interferon and Lymphokine Preparations, Journal of Immunological Methods, vol. 66, pp. 103–112, 1984.

Bishop et al. Affinity Purification of x–Galactosidase A from Human Spleen, Placenta and Plasma with Elimination of Pyrogen Contamination, The Journal of Biological Chemistry, vol. 256, No. 3, pp. 1307–1316, 1981.

(List continued on next page.)

Primary Examiner—Cecilia J. Tsang
Assistant Examiner—Anish Gupta
Attorney, Agent, or Firm—Senniger, Powers, Leavitt & Roedel

[57] ABSTRACT

During the purification of pharmaceutical grade crosslinked hemoglobin mixtures of crosslinked and uncrosslinked hemoglobin are heated in the presence of nonstoichiometric amounts of oxygen, resulting in the selective precipitation of the uncrosslinked hemoglobin. After separation of the precipitated uncrosslinked tetramers, the crosslinked hemoglobin remaining in the supernatant is so purified that a further chromatography purification step is unnecessary. This hemoglobin is highly crosslinked absolutely free of chromatography fines, and has a low methemoglobin content.

21 Claims, 2 Drawing Sheets

OTHER PUBLICATIONS

Chanutin et al. Effect of Organic and Inorganic Phosphates on the Oxygen Equilibrium of Human Erythrocytes, Archives of Biochemistry and Biophysics, 121, pp. 96–102, 1967.

Christensen et al. Preparation of Human Hemoglobin A0 for Possible Use as a Blood Substitute, Journal of Biochemical and Biophysical Methods vol. 17, pp. 143–154, 1988.

DeVenuto et al. Characteristics of Stroma–Free Hemoglobin Prepared by Crystalization, J. Lab. Clin. Med., vol. 89, No. 3, pp. 509–516, 1977.

Deloach et al. A Continuous–Flow–High–Yeild Process for Preparation of Lipid–Free Hemoglobin, Analytical Biochemistry 157, pp. 191–198, 1986.

Dixon, Gel Filtration of Haemoglobin, Biochemical Education, vol. 13, No. 4, (3 pages), 1985.

Edsall, Stabilization of Serum Albumin to Heat, and Inactivation of the Hepatitis Virus, Vox Sang., vol. 46, pp. 338–340, 1984.

Estep et al. Virus Inactivation in Hemoglobin Solutions by Heat, Biomat., Art. Cells, Art. Org., vol. 16, Nos. 1–3, pp. 129–134, 1988.

Fellowes, Comparison of the Inactivation and Antigenicity of Foot–and–Mouth–Disease Virus by Acetylethylenelmine and by Combined Effect of Ultraviolet Light and β–Propiolactone, The Journal of Immunology, vol. 95, No. 6, pp. 1100–1106, 1966.

Feola et al. Biocompatability of Hemoglobin Solutions: The Effects of Contaminants, Hemoglobin and Hemoglobin Derivatives, Biomater. Artif. Cells Immobilization Biotechnol., vol. 19, No. 2, p. 382, (abstract), 1991.

Feola et al. Quality Control of Hemoglobin Solutions. I. The Purity of Hemoglobin Before Modification, Artif. Organs, vol. 15, No. 3, pp. 243–248, 1991.

Feola et al. Stabilized Bovine Stroma–Free Hemoglobin Solution, Advances in Blood Substitute Research, Proceedings of an International Symposium, p. 429, 1982.

Feola et al. Generations of Free Oxygen Radicals and the Toxicity of Hemoglobin Solutions, Biomater. Artif. Cells, Artif. Organs, vol. 18, No. 2, pp. 189–202 (abstract), 1990.

Feola et al. Toxicity of Polymerized Hemoglobin Solutions, Surgery, Gynecology & Obstretrics, vol. 166, pp. 211–222, 1988.

Gellis et al. Chemical, Clinical, and Immunological Studies on the Products of Human Plasma Fractionation, XXXVI, Inactivation of the Virus of Homologous Serum Hepatitis in Solutions of Normal Human Serum Albumin by Means of Heat, J Clin Invest, vol. 27, pp. 239–44, 1948.

Gooding et al. HPLC of Biological Macromolecules, Chapter 1—Silica as a Support, pp. 3–7, 1990.

Grun, Bovine Viruses and Bovine Spongiform Encephalopathy Agent, (Quality Biotech Inc.) The Technology Report No. 5, 1991.

Haas et al. The Large Scale Purification of Ubiquitin from Human Erythrocytes, Preparative Biochemistry, vol. 15, Nos. 1 & 2, pp. 49–60, 1985.

Hartman et al. Combined Beta–Propiolactone and Ultraviolet Irradiation for Plasma Sterilization, Hepatitis Frontiers, Chapter 33, pp. 407–417, 1957.

Hilfenhaus et al. Inactivation of the AIDS–Causing Retrovirus and Other Human Viruses in Antihemophilic Plasma Protein Preparations by Pasteurization, Vox Sang., vol. 50, pp. 208–211, 1986.

Hilfenhaus et al. Pasteurization as an Efficient Method to Inactivate Blood Borne Viruses in Factor VIII Concentrates, Drug Res., vol. 36, No. 1, 1986.

Horowitz et al. Inactivation of Viruses in Labile Blood Derivatives, Transfusion, vol. 25, No. 6, pp. 516–522, 1985.

Issekutz, Removal of Gram–Negative Endotoxin from Solutions by Affinity Chromatography, Journal of Immunological Methods, vol. 61, pp. 275–281, 1983.

Karplus et al. A New Method for Reduction of Endotoxin Contamination from Protein Solutions, Journal of Immunological Methods, vol. 105, pp. 211–220, 1987.

Kim, Evaluation of Bovine Hemoglobin Solution as a Blood Substitute, Texas Tech University, 1983.

Kothe et al. Characterization of a Modified, Stroma–Free Hemoglobin Solution as an Oxygen–Carrying Plasma Substitute, Surgery, Gynocology and Obstertrics, vol. 161, pp. 564–569, 1985.

Kühnl et al. Reduction of Virus Load in Blood Donations by Screening Methods, Morgenthaler J–J (ed); Virus Inactivation in Plasma Products, No. 56 pp. 9–22, 1989.

Lee et al. The Purification and Comparative Analysis of Hemoglobin from Animal Bloods, Biomat., Art., Cells & Immob. Biotech., vol. 20, Nos. 2–4, pp. 477–488, 1992.

LoGrippo, Investigations of the Use of Beta–Propiolactone in Virus Inactivation, Annals New York Academy of Sciences, vol. 83, pp. 578–594, 1960.

Macdonald et al. Coronary Vasoconstrictor Activity of Purified and Modified Human Hemoglobin, Biomat., Art. Cells, Art. Org., vol. 18, No. 2, pp. 263–282, 1990.

Minobe et al. Characteristics of Immobilized Histamine for Pyrogen Adsorption, Journal of Chromatography, vol. 262, pp. 193–198, 1983.

Minobe et al. Preparation of Adsorbents for Pyrogen Adsorption, Journal of Chromotography, vol. 248, pp. 401–408, 1982.

Nelson et al. Preparation and Characterization of Diaspirin Cross–Linked Hemoglobin Solutions for Preclinical Studies, Biomater. Artif. Cells & Immob. Biotech., vol. 20, Nos. 2–4, pp. 423–427, 1992, Blood Substitutes, Oxygen Carriers, pp. 241–245, 1993.

Nelson et al. Synthesis and Properties of Polymerized, Diaspirin Cross–Linked Hemoglobins, Biomater. Artif. Cells & Immob. Biotech., vol. 20, Nos. 2–4, pp. 253–258, 1992, Blood Substitutes, Oxygen Carriers, pp. 86–91, 1995.

Pearson, Endotoxin (Chapter 3), Pyrogens in Advances in Blood Substitute Research, pp. 23–56, 1985.

Pierce Chemical Company, Detoxi–Gel Endotoxin Removing Gel, Pierce Chemical Company Handbook and General Catalog Product No. 20339, pp. 144, 1984.

Prince et al. Sterilisation of Hepatitis and HTLV–III Viruses by Exposure to TRI(n–Butyl)Phospate and Sodium Cholate, The Lancet, pp. 706–710, 1986.

Prince et al. β–Propiolactone/Ultraviolet Irradiation: A Review of Its Effectiveness for Inactivation of Viruses in Blood Derivatives, Reviews of Infectious Diseases, vol. 5, No. 1, pp. 92–107, 1983.

Pryde et al. Applications of High Performance Liquid Chromatography, pp. 20 and 53, 1979.

Schmerr et al. Preparation of Sheep and Cattle Immunoglobulins with Antibody Anctivity by High–Performance Liquid Chromatography, Journal of Chromatography, vol. 326, pp. 225–233, 1985.

Schneider et al. An Alternative Method of Large Scale Plasma Fractionation for the Isolation of Serum Albumin, Blut, Band 30, pp. 121–134, 1975.

Sheefield et al. Preparation and in vivo Evaluation of Two Bovine Hemoglobin–Based Plasma Expanders, Biotechnology and Applied Biochemistry, vol. 12, pp. 630–642.

Simoni et al. Anion–Exchange HPLC Does Not Completely Purify Hemoglobin from Other Proteins and Other Peptides, Biomater. Artif. Cells Immobilization Biotechnol., vol. 19, No. 2, p. 488, (abstract), 1991.

Simoni et al. Evaluation of Anion–Exchange Liquid Chromatography for Purification of Hemoglobin from Peptides and Other Proteins, Analytica Chimica Acta, vol. 249, pp. 169–183, 1991.

Sofer, Chromatographic Removal of Pyrogens, Biotechnology, vol. 12, No. 2, pp. 1035–1038, 1984.

Stryer, Exploring Proteins, Biochemistry, Third Edition, pp. 46–49, 1988.

Suomela et al. High–Performance Liquid Chromatography in the Quality Control of Immunoglobin Preparations During Production and Storage, Journal of Chromatography, vol. 297, pp. 369–373, 1984.

White et al. Toxicity of Human Hemoglobin Solution Infused into Rabbits, J. Lab. Clin. Med., vol. 108, pp. 121–131, 1986.

Yost et al. Practical Liquid Chromatography An Introduction, Chapter 1.4, pp. 13–21, 1980.

PREPARATION OF PHARMACEUTICAL GRADE HEMOGLOBINS BY HEAT TREATMENT IN PARTIALLY OXYGENATED FORM

BACKGROUND OF THE INVENTION

The use of free hemoglobin in treating a wide number of clinical conditions otherwise requiring transfusion of whole blood has been proposed over many years. For an historical review, see Winslow, *Hemoglobin-based Red Cell Substitutes*, Johns Hopkins U. Press (1992). Several of the obstacles to the use of free hemoglobin have included the toxicity of native hemoglobin upon dissociation into subunits, and the higher binding affinity of free hemoglobin for oxygen thus limiting oxygen release capabilities in the tissues. Further obstacles have been achieving a hemoglobin preparation free of cellular stroma, viral and bacterial pathogens, and endotoxin.

The first of these obstacles relating to unfavorable dissociation has largely been removed by utilizing various methods of crosslinking tetrameric hemoglobin. This serves the purpose of physically preventing the tetrameric subunits from dissociating into alpha-beta dimers. U.S. Pat. No. 4,061,736 (Bonson, et al.) describes intramolecularly crosslinked hemoglobin in which the crosslinking agent is either a heterocyclic triazine or a halogenated aromatic, cycloalkane, dialdehyde, etc. In U.S. Pat. No. 4,826,811 (Sehgal, et al.), hemoglobin is first pyridoxylated and then intramolecularly and intermolecularly crosslinked with glutaraldehyde.

Other crosslinking strategies combine the objectives of conformational immobilization and molecular stability with nonantigenicity by utilizing crosslinkers having low immunogenicity. For example, U.S. Pat. No. 4,377,512 (Ajisaki, et al.) discloses crosslinking through a polyalkylene oxide linking group. U.S. Pat. No. 5,234,903 similarly discloses conjugation of hemoglobin to a polyalkylene oxide through a urethane linkage. Finally, a strategy which accomplishes all of the foregoing objectives in addition to obtaining high yields utilizing cost effective reagents, involves diaspirin crosslinking according to U.S. Pat. Nos. 4,598,064 and 4,600,531.

Another obstacle to achieving a therapeutically acceptable hemoglobin is purity. The concept of product purity refers in part to the removal of endogenous contaminants such as red blood cell stroma and nonhemoglobin proteins which are removed from the hemoglobin solution. Purity also refers to the absence of extraneously introduced contaminants such as viruses, bacteria, and endotoxins.

A great number of purification schemes have been devised to purify hemoglobin. The larger cellular components resulting from cell lysis are typically removed by filtration. The filter may be diatomaceous earth (See U.S. Pat. No. 4,001,200, Bonson) or, more typically, a small pore size membrane filter (for example, U.S. Pat. Nos. 4,001,200, 3,991,181, and 4,473,494). Generally, a crude filtration step may be followed by ultrafiltration, e.g. through a hemodialysis filter cartridge as taught in U.S. Pat. Nos. 4,598,064 and 4,401,652. Alternatively, large debris and particulate matter may be removed by continuous flow centrifugation. Early stage purification has generally improved and overcome historical difficulties in direct proportion to improvements in the filtration art, so that at present conventionally available filtration technologies are adequate for removing particulate matter in most pharmaceutical applications.

Further purification to remove nonhemoglobin soluble proteins and other materials is typically carried out by some form of gel filtration or ion exchange chromatography. By selecting an appropriate gel exclusion chromatography step, the removal of nonhemoglobin soluble proteins can be effected. For example, U.S. Pat. No. 4,136,093 (Bonhard) discloses a method of purifying filtered hemoglobin by passing through a gel filtration column of G-150 Sephadex. A much higher level of purity, said to reduce endotoxin levels to pharmacologically acceptable levels lower than 0.5 EU/mL, utilizes a double step rechromatography on Sephadex G-200, followed optionally by a haptoglobin affinity chromatography step (See U.S. Pat. Nos. 5,084,558 and 5,296,465).

Another approach to purification involves differential precipitation of proteins, reflecting the observation that in a complex mixture, some proteins are more stable to stressed conditions than others. In heating protein mixtures, it has been found that individual proteins will denature and precipitate out of solution at characteristic temperatures. Removal of the resulting precipitate comprising denatured proteins thus effects a partial purification. U.S. Pat. No. 4,861,867 discloses the differential inactivation of viruses in a hemoglobin solution by heating it in a deoxyhemoglobin form to a temperature between 45 degrees and 85 degrees Centigrade. Viruses are much more heat labile than hemoglobin, and reduction in virus titer by many logs is readily obtained upon heat treatment without appreciable loss of biologically active hemoglobin.

U.S. Pat. No. 4,861,867 discloses a heat treatment process in which deoxyhemoglobin is purified from nonhemoglobin proteins by heating the solution to a temperature between 45 degrees and 85 degrees Centigrade for varying times up to ten hours. Since it is important to limit conversion of hemoglobin to methemoglobin, deoxygenation is carried out either in the presence of reducing agents such as ascorbate, or by degassing procedures utilizing membrane gas exchange devices to effect essentially complete deoxygenation. In a typical run, 5 hours' heat treatment at 60° C. resulted in a 93% recovery of total hemoglobin.

Another object of the production of hemoglobin based blood substitutes is the manufacture of material which has low levels of the inactive oxidized methemoglobin form of this protein. This is often accomplished by performing manufacturing operations at low temperatures, since methemoglobin formation is substantially accelerated as the temperature is increased. When exposure to elevated temperature is required, such as during the reaction of hemoglobin with certain modifying agents, or during heat treatment to inactivate viruses, deoxygenation of the protein may be used to inhibit methemoglobin formation as disclosed in U.S. Pat. No. 4,861,867. On the basis of the literature pertaining to hemoglobin oxidation, a condition to be avoided is the exposure of hemoglobin to partially oxygenating conditions, since the rate of methemoglobin formation is greatest when the hemoglobin is partially saturated with oxygen. See Brooks. *Proc. Roy. Soc. Lond. Ser. B.* 118:560–577, 1935, which teaches that the rate of hemoglobin oxidation is maximal at an oxygen pressure of 20 mm Hg.

SUMMARY OF THE INVENTION

' It is an object of the present invention to provide a hemoglobin composition of pharmaceutical quality which is crosslinked to maintain the optimal oxygen binding affinity, contains less than 0.25 EU/mL of endotoxin so as not to produce an adverse physiologic reaction, is substantially free of nonhemoglobin proteins and uncrosslinked hemoglobin, is absolutely free of chromatography fines or other contaminating polymer species derived from a chromatography matrix, is substantially free of virus contamination and has a methemoglobin content of less than 5 percent at the time of product release for distribution.

It is a further object to provide a method of producing such hemoglobin comprising batch procedures which do not involve an expensive and cumbersome solid phase chromatography system.

In the present invention, solutions containing a mixture of crosslinked and uncrosslinked hemoglobin are heated to between about 45° C. and 85° C. for a period ranging from thirty minutes to ten hours in the presence of nonstoichiometric amounts of oxygen at a pH of 7.25–7.55. Upon removal of the precipitated nonhemoglobin proteins and the bulk of uncrosslinked hemoglobin, the resulting crosslinked hemoglobin solution contains less than one percent uncrosslinked material.

The composition of the present invention is a highly purified, pharmaceutically acceptable crosslinked hemoglobin solution having less than one percent residual uncrosslinked hemoglobin, trace amounts of residual non-hemoglobin proteins (less than 0.01% w/w), less than 0.25 EU/mL of endotoxin, being absolutely free of chromatography fines, or other carryover residuals from matrix-containing purification systems, and having a methemoglobin content of less than 5 percent at the time of product release for distribution.

In the method of the invention, a mixture of crosslinked and uncrosslinked deoxygenated stroma-free hemoglobin is placed in an oxygen impermeable reactor means, partially reacted with oxygen to obtain 11 to 28 percent oxyhemoglobin, heated to a temperature of between about 45° C. and 85° C., differentially or preferentially precipitating the uncrosslinked hemoglobin, and removing the precipitated uncrosslinked hemoglobin.

Equivalently, the level of partial oxygenation which can achieve the purification objective of the present invention may conveniently be measured as parts per million (ppm) of dissolved oxygen. Accordingly, a pharmaceutical grade hemoglobin may be obtained without a chromatographic purification step by placing a mixture of deoxygenated stroma free crosslinked hemoglobin and uncrosslinked hemoglobin in oxygen impermeable reactor means, introducing oxygen to a dissolved oxygen content of 0.7 to 1.7 ppm, heating the hemoglobin to a temperature of about 45° C. to 85° C., and removing the precipitated nonhemoglobin and uncrosslinked hemoglobin.

DETAILED DESCRIPTION OF THE PREFERRED EMBODIMENT

Figure 1:
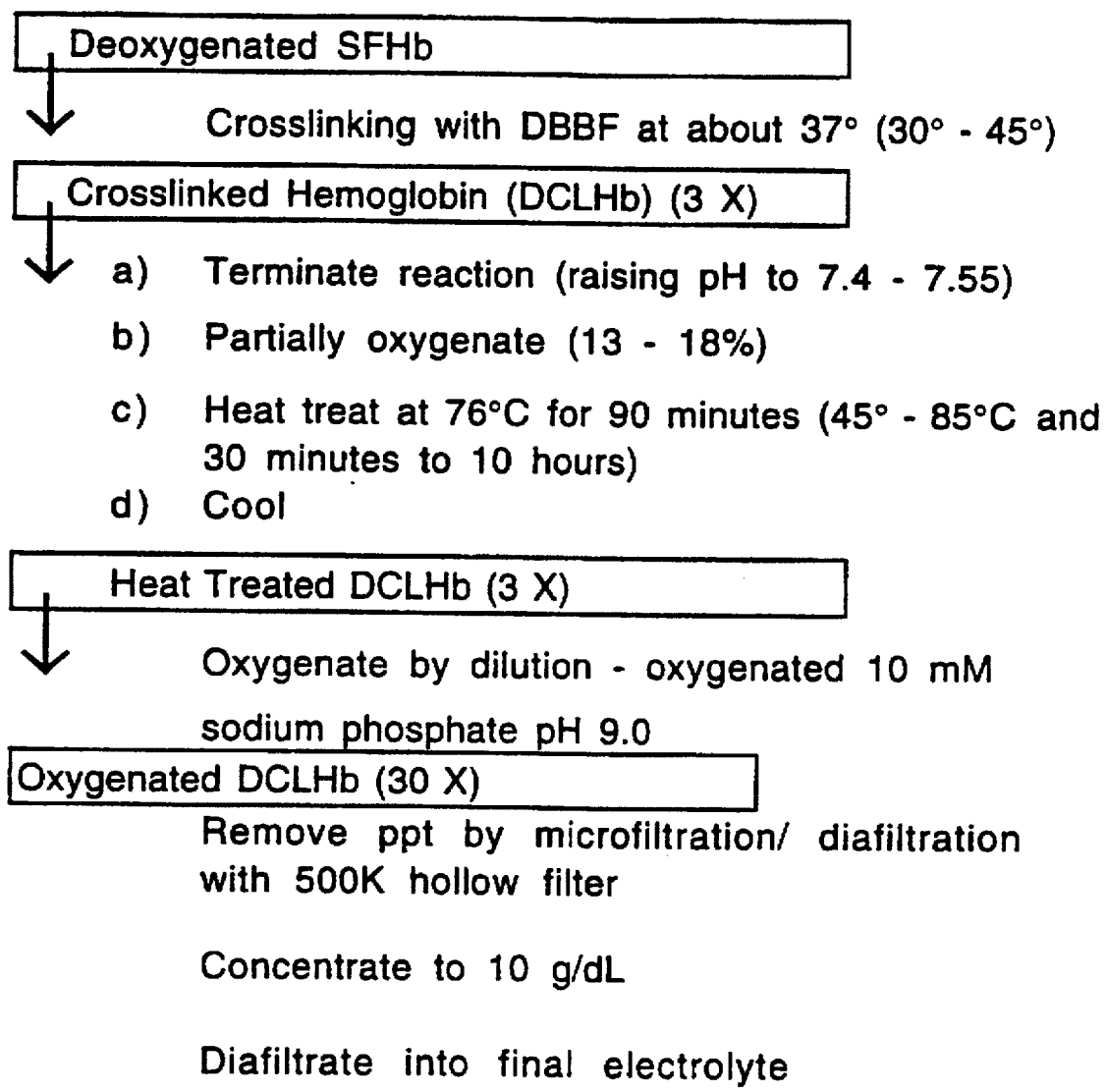
FIG. 1 is a flow diagram of the crosslinking and heat treatment steps for producing pharmaceutical grade crosslinked hemoglobin.

It has long been known that free human and some other hemoglobin released from disrupted red blood cells has a significantly higher binding affinity for oxygen than in its natural counterpart in the red cell. This high affinity binding makes the hemoglobin less useful as an oxygen carrying molecule because of its poor release properties in the tissues.

It was subsequently discovered that crosslinking with certain agents forces the hemoglobin tetramer into a conformation in which the binding affinity of oxygen approximates that of intact red cells. The acceptable $P_{50}$ values ( the oxygen partial pressure at which the hemoglobin is half saturated) for the crosslinked hemoglobins of the present invention are between 20 and 45 mm Hg inclusive. The crosslinking also stabilizes the tetrameric hemoglobin which otherwise tends to dissociate into dimers. Also within the scope of this invention are crosslinked hemoglobins which have been further polymerized to produce macromolecules ranging from 120,000 to 600,000 Daltons in molecular weight.

The acellular hemoglobin utilized in the present invention may be of any type which is stroma-free and modified chemically to prevent subunit dissociation and to increase the oxygen binding affinity to the range of $P_{50}$ values between about 20 and 45 mm Hg as long as the chemical bonds formed are stable to heating under the conditions noted in the following. The modified hemoglobin may be a conjugated hemoglobin, crosslinked hemoglobin, polymerized hemoglobin.

Several examples of hemoglobin modification technology have been described in the scientific literature which may be used to advantage in the practice of the present invention. For example, see the review contained in Winslow, R.M., *Hemoglobin-based Red Cell Substitutes*, The John Hopkins U. Press (1992). More specifically, the methods of making chemically modified hemoglobin are set forth hereinafter.

A conjugated hemoglobin is one to which a non-protein macromolecule is bound covalently to hemoglobin. One example is a hemoglobin chemical modified by poly-alkylene glycol, which is described together with a process for its preparation in WO 9107190 (Enzon). An example of a hemoglobin conjugated to poly(alkylene oxide) and a process for its preparation are provided in U.S. Pat. Nos. 4,301,144, 4,412,989 and 4,670,417, and in Japanese Patent Nos. 59-104323 and 61-053223 (Ajinomoto). Hemoglobin may be conjugated to inulin in a process disclosed in U.S. Pat. No. 4,377,512 (Ajinomoto). PCT application no. 91/07190, U.S. Pat. Nos. 4,301,144, 4,670,412, 4,377,512 and Japanese Patent Nos. 59-104323 and 61-053223, are hereby incorporated by reference.

A crosslinked hemoglobin contains an intramolecular chemical link. Examples of crosslinked hemoglobins and methods for their preparation are described in U.S. Pat. Nos. 4,001,401 and 4,053,590, which disclose intramolecular crosslinking between an alpha and beta subunit of a hemoglobin tetramer utilizing compounds such as halogenated cycloalkanes, diepoxides, and diazobenzidines. In the present heat treatment purification method, a preferred modified hemoglobin is crosslinked with bis(3,5-dibromosalicyl)fumarate to create a fumarate crosslink between the two alpha subunits. This crosslinked hemoglobin is more fully described, together with methods for its preparation, in U.S. Pat. Nos. 4,598,064, 4,600,531, RE 34,271, omitting the chromatography step. It is preferably manufactured under the conditions disclosed in U.S. Pat. No. 5 5,128,452 (Hai) to prevent crosslinking between β chains. U.S. Pat. Nos. 4,598,064, 4,600,531, RE 34,271 and 5,128,452 are hereby incorporated by reference. PCT application no. 90/13309; (Staat Der Nederlanden De Minister Van Defeuric) discloses a method for crosslinking hemoglobin through a β-β linkage.

A polymerized hemoglobin is one in which intermolecular cross-linking of hemoglobin tetramers has been used to increase the molecular weight of the modified hemoglobin.

An example of a polymerized hemoglobin and a process for its preparation are described in U.S. pending applications Ser. Nos. 08/149,679, 08/173,882, 08/480,593 and 08/473,459; U.S. Pat. No. 4,777,244 discloses a method for crosslinking and polymerizing with aliphatic dialdehydes. The foregoing patents are hereby incorporated by reference.

A hemoglobin that has been modified by a combination of methods is exemplified by the following. Hemoglobins modified by pyridoxal-5'-phosphate to adjust the oxygen affinity and by polyethylene glycol conjugation and processes for its preparation are described in Japanese Patent Nos. 59-089629, 59-103322 and 59-104323 (Ajinomoto). U.S. Pat. No. 5,248,766 discloses a crosslinking polymerizing strategy and a process for covalently interconnecting tetrameric units with oxiranes to form polyhemoglobins with molecular weights in excess of 120,000 Daltons. The foregoing patents disclosing polymerized hemoglobins, U.S. Pat. Nos. 5,194,590, 5,248,766, Japanese Patent Nos. 59-103322, 59-089629 and 59-104323, are hereby incorporated by reference.

Hemoglobin may be modified by site-directed mutagenesis and expressed in micro-organisms or transgenic animals. Recombinant mutant and artificial hemoglobin and its production in cell cultures or fluids is described in U.S. Pat. No. 5,028,588 (Somatogen). Di-alpha and di-beta globin-like polypeptide(s) used for production of hemoglobin in bacteria and yeast are described in PCT application no. 90/13645 (Somatogen). A non-natural multimeric hemoglobin-like protein is described in PCT application no. 93/09143 (Somatogen). In general any method of crosslinking, polymerizing, encapsulating or genetically modifying, or combination thereof which yields a free tetramer having a $P_{50}$ in the operative range of 20 to 45 mm Hg will have efficacy in the present method. Conditions may be adjusted for each such crosslinked tetramer or polymer derived therefrom without undue experimentation.

FIG. 1 is a flow diagram for the manufacturing process involved in producing pharmaceutical grade diaspirin crosslinked hemoglobin, hereinafter referred to as "DCLHb™." While other crosslinked hemoglobins may be purified in a similar process, DCLHb™ manufacture is described herein in detail as a preferred embodiment. Its preferred status reflects its ease of synthesis and purification in commercial large-scale quantities, and its utility as a therapeutic agent in several indications.

Red blood cells are pooled, washed to reduce the residual level of plasma proteins by methods such as constant volume diafiltration and concentrated. The washed cells are lysed in three volumes of hypotonic buffer. The resulting hemolysate is filtered using a 500K pore size fiber membrane to produce a stroma-free hemoglobin solution. The stroma free hemoglobin is concentrated by ultrafiltration. This solution is filtered through a 0.2 micron pore size filter.

Stroma-free hemoglobin is then deoxygenated in the presence of sodium tripolyphosphate (0.01M). Oxyhemoglobin content of the solution is reduced to less than three percent. It is important to remove oxygen to a low level to establish a baseline, since the readdition of oxygen, which is critical to the present process, requires precise determination. After deoxygenation, the hemoglobin is crosslinked with a stoichiometric excess of bis(3,5-dibromosalicyl) fumarate (DBBF).

At this point, oxygen is introduced into the reactor and the solution at a concentration of about 5–6 g/dL is then heated to about 76° C. for 90 minutes at a pH of 7.4 in a typical run. The range of temperatures and duration of heat treatment which may be utilized are 45° C. to 85° C. for 30 minutes to 10 hours, respectively. Within this range, 65° C. to 80° C. is preferred, and 74° C. to 78° C. is most preferred. The concentration of hemoglobin may vary from 3 g/dL to 20 g/dL. The pH may be varied from 7.25 to 7.55. In selecting conditions within the stated ranges, some experimentation will be required to optimize yields while maintaining a high level of purity. For example, if a shorter processing time is desired, heat treatment will be carried out at a temperature greater than 76° C.; however, some adjustment of concentration or pH may be required. It will not involve more than a few production runs to obtain specifications for optimum production within each of the stated ranges. The oxygen content may be measured according to two parameters. Oxygen is added until the total oxyhemoglobin content is between about 11 and 28 percent, preferably about 13 to 18 percent. Alternatively, the percent of dissolved oxygen in the hemoglobin solution may be measured. The dissolved oxygen content should be maintained between about 0.7 and 1.7 ppm. FIG. 1 shows a typical sequence of steps for crosslinking and heat treating the hemoglobin. The diagram gives the parameters in a preferred embodiment. However, times and temperature of treatment may be varied. In general, the higher the temperature of treatment, the less time is required to complete the process. However, for any particular modified hemoglobin, the temperature must be kept below the denaturation temperature for the desired protein being heat treated under these conditions. In this regard 85° C. may be too high for DCLHb under these conditions, but acceptable for other derivatives.

Process control in the heat treatment step is critical. While construction of special equipment is unnecessary, the integrity of the system with respect to atmosphere and dissolved gas control must not be compromised. It is essential that the reaction vessels be gas-impermeable and precautions taken that no leak occurs. Precision valves should be employed to prevent gasket leaks and to ensure precise metering of oxygen.

The dissolved oxygen level must be meticulously controlled in the 0.7–1.2 ppm range (11–28% oxyhemoglobin) during the heat treatment step. Under these conditions, the level of methemoglobin is less than 1 percent post-heat treatment, and remains low < 5%) upon packaging and product release. Keeping these methemoglobin levels low during the manufacturing process makes it statistically unlikely that any batch will exceed the 5% limit for release of product to distribution.

It has been determined empirically that the uncrosslinked hemoglobin precipitates preferentially, particularly when partially oxygenated. Since the uncrosslinked hemoglobin binds oxygen more tightly than the crosslinked molecules, it may be expected that the uncrosslinked material is preferentially oxygenated. However, Applicants have no explanation for the finding that, while uncrosslinked hemoglobin comprises upwardly 30% or more of total hemoglobin, the operable range of oxyhemoglobin content is 11 to 28 percent. The oxygen content is thus nonstoichiometric, and addition of more oxygen leads to a drastic reduction in yield. It was surprising to find that a more highly purified crosslinked hemoglobin preparation could be obtained by partially reoxygenating reaction mixtures prior to heat treatment at elevated temperatures in view of the teachings in Brooks supra. The solution obtained after heat treatment after partial reoxygenation contained less than 2% of the undesirable non-crosslinked hemoglobin, but the soluble crosslinked protein was not highly oxidized. This represents a significant improvement in chemical purity over the material resulting from heat treatment of reaction mixtures which were more completely deoxygenated, as the latter contained several percent or greater uncrosslinked hemoglobin. The result is even more surprising in light of the fact that the optimal amount of oxygen present in solution prior to the initiation of heat treatment is insufficient to fully saturate the uncrosslinked hemoglobin which is present. The invention therefore enables enhanced purification of crosslinked hemoglobin from reaction mixtures containing substantial amounts of non-crosslinked hemoglobin without increasing the level of methemoglobin in the final crosslinked product.

Figure 2:
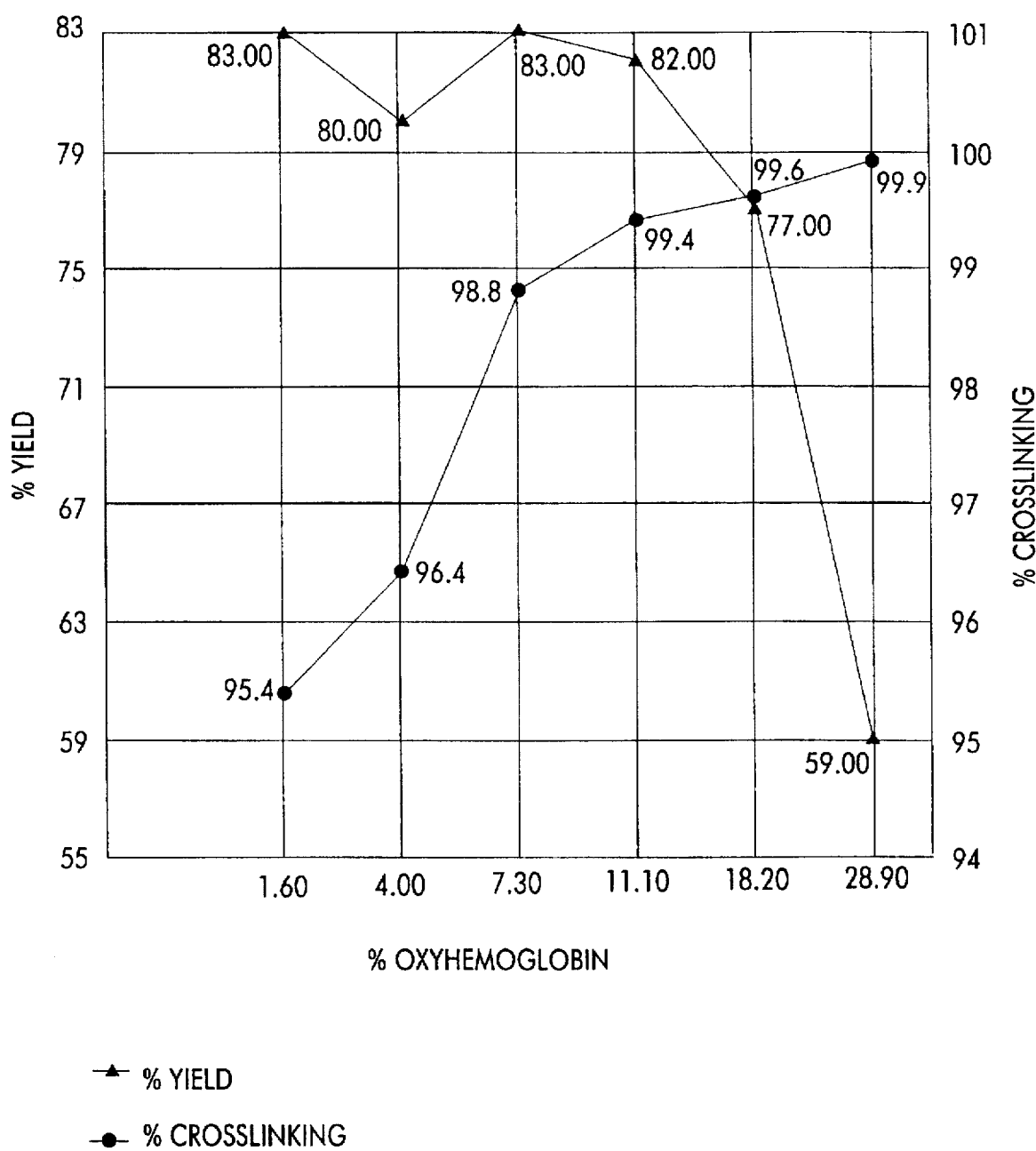
FIG. 2 is a rectilinear plot of crosslinked hemoglobin yields as a function of percent oxyhemoglobin present during the heat treatment step of the manufacturing process.

FIG. 2 shows the effect of varying oxyhemoglobin content on product yields. As oxygen content increases, the percent crosslinking increases, but if the specified range is exceeded, the yields begin to drop. The operable range is from about 11 to about 28 percent, preferably 13 to 18 percent oxyhemoglobin corresponding to 0.7 to 1.7 ppm dissolved oxygen.

Heat treatment may be carried out in the temperature range from 45° C. to 85° C., and the temperature may be varied within this range over a total treatment time of thirty minutes to ten hours. There is a generally reciprocal relation between time and temperature, less time being required for treatment at higher temperatures. Heating for about 90 minutes at 76° C. has been determined empirically as being especially well adapted to large scale manufacturing purposes. Heat treatment should continue for a time sufficient to obtain optimum precipitation of the uncrosslinked hemoglobin for the particular temperature selected within the 45–85° C. range.

Following heat treatment, the precipitate is removed through a series of conventional filtration steps, or by centrifugation. Concentration of DCLHb™ is facilitated by diafiltration (as, for example, against a Millipore 30K spiral ultrafilter).

The crosslinked hemoglobin produced by the process described hereinabove is compositionally distinctive and unique. The levels of purity attained make a chromatography step unnecessary. This has a profound effect on cost, as preparative chromatography in a manufacturing context is very expensive and wasteful of resins or gels, since the matrix beds are not readily reconstituted. Also chromatography fines will appear in the final product, and if not actually present in amounts rendering the product adulterated, may cause ambiguous or false positive quality assurance tests, as, for example with the LAL test for endotoxin.

In addition to the extremely low percentage of uncrosslinked hemoglobin and nonhemoglobin proteins, and the absolute absence of chromatography fines, the crosslinked hemoglobin of the present invention has an endotoxin level of less than 0.25 EU/mL, as measured by the test described in USP chapter 85 and a methemoglobin content of less than 5 percent at the time of product release. In the manufacturing process, sources of endotoxin are rigorously excluded, so that ultrapure water and reagents are used. The equipment is pharmaceutically robust in design and is engineered to permit thorough cleaning. The design specifications for such a facility will be known by those skilled in the pharmaceutical engineering art.

Further advantages of the present invention will be apparent from the Example which follows.

EXAMPLE

The heat treatment procedure was performed on reaction mixtures obtained by reacting DBBF with human stroma-free hemoglobin under varying conditions. Table 1 shows the effect on yields and percent crosslinked hemoglobin in the final product of varying amounts of oxygen present during heat treatment. In all situations the stroma-free hemoglobin was thoroughly deoxygenated prior to crosslinking and then reoxygenated to varying degrees prior to heat treatment. The results show that at levels of oxyhemoglobin greater than 28 percent, yields fall from the 77–83% range to only 59%, with only marginal increase in the purity of the final product with respect to residual uncrosslinked hemoglobin (99.6% to 99.9%). From these data it is clear that the introduction of oxygen to attain between about 11 and 18 percent oxyhemoglobin is desirable to achieve the maximum yields with high purity and maintain methemoglobin levels low.

TABLE 1

Effects of Heat Treatment in the Presence of Some Oxygen

| Experimental Parameter | Very Low D.O. | Low D.O. | Mid Range D.O. | High D.O. | Very High D.O. | Super High D.O. |
|---|---|---|---|---|---|---|
| Prior to Heat Treatment | | | | | | |
| ppm Oxygen (O$_2$)* | 0.08 | 0.2 | 0.8 | 1.1 | 1.6 | — |
| % Oxyhemoglobin | 1.6 | 4.0 | 7.3 | 11.1 | 18.2 | 28.9 |
| Total Hemoglobin (g/dL) | 6.3 | 6.4 | 6.3 | 6.3 | 6.4 | 4.6 |
| % Methemoglobin | 0 | 0 | 0 | 0 | 0.4 | 0.5 |
| pH at 37° C. | 7.35 | 7.40 | 7.38 | 7.47 | 7.35 | 7.48 |
| % Crosslinking | 72 | 72 | 72 | 72 | 72 | 73 |
| During Heat Treatment | | | | | | |
| Temp Ramp Time (min) | 64 | 66 | 64 | 62 | 66 | 65 |
| pH at 76° | 6.81 | 6.89 | 6.85 | 6.89 | 6.85 | — |
| Cooling Time (min) | 64 | 67 | 64 | 60 | 65 | 70 |
| Post Heat Treatment | | | | | | |
| % Volume Recovered | 76 | 74 | 75 | 72 | 77 | 82 |
| Total Hemoglobin (g/dL) | 5.2 | 5.2 | 5.1 | 5.2 | 4.6 | 2.4 |
| % Methemoglobin | 2.2 | 3.1 | 3.5 | 2.4 | 0.2 | 2.0 |
| % Yield (DCLHb recovered) | 83 | 80 | 83 | 82 | 77 | 59 |
| % Crosslinking | 95.4 | 96.4 | 98.8 | 99.4 | 99.6 | 99.9 |

*Accurate reading not available.

A. The in-process method for determination of percent crosslinking in unheated reaction mixtures was determined using a Bio-Sil ™ TSK 250 column and 1M MgCl$_2$ in BisTris buffer, pH 7.2, as a mobile phase.

B. The percent yield was calculated as:

$$\% \text{ Yield} = \frac{\text{THb Final} \times \% \text{ Crosslinked}}{\text{THb Initial} \times 72} \times \frac{\% \text{ Volume Recovered}}{100}$$

C. The percent crosslinking in the heat treated solution was determined using a Superose ™ 12 column and 0.75M MgCl$_2$ in BisTris buffer, pH 6.5, as a mobile phase.

Table 2A and 2B compare the methemoglobin values at product release before the microoxygenation step was implemented in the process (2A) with the corresponding values after implementation of microoxygenation (2B). The average of values prior to microoxygenation was 4.09 percent compared to only 1.6 percent after implementation of microoxygenation.

TABLE 2A

METHEMOGLOBIN VALUES FROM PRODUCTION RUNS PRIOR TO INTRODUCTION OF THE MICROOXYGENATION STEP

| Lot No. | Release % MetHb |
|---|---|
| PBS-1-90-010 | 4.3 |
| PBS-1-91-006 | 4.9 |
| PBS-1-91-007 | 3.9 |
| PBS-1-91-008 | 1.5 |
| PBS-2-92-001 | 4.1 |
| HBXR-92-128 | 4.1 |
| HBXR-92-149 | 2.9 |
| HBXR-92-170 | 2.3 |
| HBXR-92-198 | 3.6 |
| HBXR-92-268 | 2.9 |
| PBS-2-93-001 | 4.9 |
| PBS-2-93-013 | 3.7 |
| HBXR-93-070 | 3.7 |
| HBXR-93-210 | 4.5 |
| HBXR-93-259 | 4.0 |
| HBXR-93-308 | 3.9 |
| HBXR-93-343 | 4.1 |
| HBXR-94-055 | 5.5 |
| HBXR-94-097 | 5.8 |
| PBS-2-94-016 | 5.2 |
| AVERAGE: | 4.0 |

For the latter, note the consistency of values below 1 percent for bulk sterile batches and less than 50 percent for all release batches. Statistically there is a 95% confidence that 99% of all batches manufactured according to the present process will have release values of methemoglobin of less than the targeted 5 percent. A level of less than 1 percent methemoglobin immediately after heat treatment is a strong indicator (although not necessarily a causal one) that the methemoglobin level will conform to the less than 5 percent standard at product release.

TABLE 2B

METHEMOGLOBIN VALUES FROM PRODUCTION RUNS AFTER INTRODUCTION OF THE MICROOXYGENATION STEP

| Lot No. | Release % MetHb |
|---|---|
| HBXR-94-230 | 1.0 |
| PBS-2-94-023 | 2.1 |
| HBXR-94-314 | 1.8 |
| HBXR-94-342 | 1.5 |
| HBXR-95-026 | 2.4 |
| HBXR-95-061 | 1.5 |
| HBXR-95-096 | 1.1 |
| AVERAGE: | 1.6 | n.d.- None detected

What is claimed is:

1. A method for preparing pharmaceutical grade hemoglobin comprising:
   adding oxygen to a hemoglobin mixture comprising crosslinked hemoglobin and uncrosslinked hemoglobin to form a reaction mixture, the reaction mixture containing from about 11 to about 28% oxyhemoglobin or having a dissolved oxygen content of about 0.7 to about 1.7 ppm;
   heating the reaction mixture to form a precipitate containing the uncrosslinked hemoglobin; and
   removing the precipitate.

2. A method according to claim 1 wherein the crosslinked hemoglobin and uncrosslinked hemoglobin are predominantly deoxygenated hemoglobin.

3. A method according to claim 1 wherein the pharmaceutical grade hemoglobin contains less than 5% methemoglobin.

4. A method according to claim 1 wherein the pharmaceutical grade hemoglobin is stroma-free, substantially free of nonhemoglobin proteins and viral contamination, and has a $P_{50}$ of from about 20 to about 45 mm Hg.

5. A method according to claim 1 wherein the crosslinked hemoglobin is diaspirin-crosslinked hemoglobin.

6. A method according to claim 1 wherein the reaction mixture is heated to a temperature between about 45° C. and about 85° C.

7. A method according to claim 6 wherein the reaction mixture is heated to a temperature between 65° C. and 80° C.

8. A method according to claim 7 wherein the reaction mixture is heated to a temperature between 74° C. and 78° C.

9. A method according to claim 6 wherein the reaction mixture is heated for 30 minutes to 10 hours.

10. A method according to claim 9 wherein the reaction mixture has a pH of 7.25 to 7.55 and a hemoglobin concentration of 3 to 20 g/dl.

11. A method for preparing pharmaceutical grade hemoglobin comprising:
    adding oxygen to a hemoglobin mixture comprising chemically-modified hemoglobin and chemically-unmodified hemoglobin to form a reaction mixture, the reaction mixture containing from about 11 to about 28% oxyhemoglobin or having a dissolved oxygen content of about 0.7 to about 1.7 ppm;
    heating the reaction mixture to form a precipitate containing the chemically-unmodified hemoglobin; and
    removing the precipitate.

12. A method according to claim 11 wherein the chemically-modified hemoglobin and the chemically-unmodified hemoglobin are predominantly deoxygenated hemoglobin.

13. A method according to claim 11 wherein the pharmaceutical grade hemoglobin contains less than 5% methemoglobin.

14. A method according to claim 11 wherein the pharmaceutical grade hemoglobin is stroma-free, substantially free of nonhemoglobin proteins and viral contamination, and has a $P_{50}$ of from about 20 to about 45 mm Hg.

15. A method according to claim 11 wherein the chemically-modified hemoglobin is crosslinked, polymerized, encapsulated or conjugated hemoglobin.

16. A method according to claim 15 wherein the chemically-modified hemoglobin is diaspirin-crosslinked hemoglobin.

17. A method according to claim 11 wherein the reaction mixture is heated to a temperature between about 45° C. and about 85° C.

18. A method according to claim 17 wherein the reaction mixture is heated to a temperature between 65° C. and 80° C.

19. A method according to claim 18 wherein the reaction mixture is heated to a temperature between 74° C. and 78° C.

20. A method according to claim 17 wherein the reaction mixture is heated for 30 minutes to 10 hours.

21. A method according to claim 20 wherein the reaction mixture has a pH of 7.25 to 7.55 and a hemoglobin concentration of 3 to 20g/dl.

* * * * *